(12) United States Patent
Fischer et al.

(10) Patent No.: US 8,816,097 B2
(45) Date of Patent: Aug. 26, 2014

(54) ACTIVE INGREDIENT COMBINATIONS HAVING INSECTICIDE AND ACARICIDE PROPERTIES

(75) Inventors: Reiner Fischer, Monheim (DE); Wolfram Andersch, Bergisch Gladbach (DE); Thomas Bretschneider, Lohmar (DE); Anton Kraus, Leichlingen (DE); Heike Hungenberg, Langenfeld (DE); Olga Malsam, Rösrath (DE)

(73) Assignee: Bayer CropScience AG, Monheim (DE)

( * ) Notice: Subject to any disclaimer, the term of this patent is extended or adjusted under 35 U.S.C. 154(b) by 715 days.

(21) Appl. No.: 12/373,648

(22) PCT Filed: Jul. 11, 2007

(86) PCT No.: PCT/EP2007/006133
§ 371 (c)(1),
(2), (4) Date: Dec. 4, 2009

(87) PCT Pub. No.: WO2008/009379
PCT Pub. Date: Jan. 24, 2008

(65) Prior Publication Data
US 2010/0130578 A1    May 27, 2010

(30) Foreign Application Priority Data
Jul. 18, 2006   (DE) .......................... 10 2006 033 154

(51) Int. Cl.
*A01N 37/42* (2006.01)
(52) U.S. Cl.
CPC ..................................... *A01N 37/42* (2013.01)
USPC ........................................ 548/408; 514/409
(58) Field of Classification Search
CPC ..................................................... A01N 37/42
USPC .......................................... 548/408; 514/409
See application file for complete search history.

(56) References Cited

U.S. PATENT DOCUMENTS

| | | | |
|---|---|---|---|
| 5,258,527 A | 11/1993 | Krauskopf et al. |
| 5,262,383 A | 11/1993 | Fischer et al. |
| 5,462,913 A | 10/1995 | Fischer et al. |
| 5,504,057 A | 4/1996 | Fischer et al. |
| 5,567,671 A | 10/1996 | Fischer et al. |
| 5,589,469 A | 12/1996 | Fischer et al. |
| 5,610,122 A | 3/1997 | Fischer et al. |
| 5,622,917 A | 4/1997 | Fischer et al. |
| 5,683,965 A | 11/1997 | Bachmann et al. |
| 5,830,825 A | 11/1998 | Fischer et al. |
| 5,830,826 A | 11/1998 | Fischer et al. |
| 5,945,444 A | 8/1999 | Fischer et al. |
| 5,994,274 A | 11/1999 | Fischer et al. |
| 6,110,872 A | 8/2000 | Lieb et al. |
| 6,114,374 A | 9/2000 | Lieb et al. |
| 6,133,296 A | 10/2000 | Lieb et al. |
| 6,140,358 A | 10/2000 | Lieb et al. |
| 6,187,944 B1 | 2/2001 | Koyanagi et al. |
| 6,200,932 B1 | 3/2001 | Fischer et al. |
| 6,251,830 B1 | 6/2001 | Fischer et al. |
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,417,370 B1 | 7/2002 | Lieb et al. |
| 6,436,988 B1 | 8/2002 | Wachendorff-Neumann |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,511,942 B1 | 1/2003 | Lieb et al. |
| 6,576,661 B1 | 6/2003 | Brück et al. |
| 6,589,976 B1 | 7/2003 | Fischer et al. |
| 6,608,211 B1 | 8/2003 | Hagemann et al. |
| 6,861,391 B1 | 3/2005 | Fischer et al. |
| 6,894,005 B1 | 5/2005 | Maetzke et al. |
| 6,899,886 B2 | 5/2005 | Takahashi et al. |
| 7,718,186 B2 | 5/2010 | Fischer et al. |
| 8,202,875 B2 | 6/2012 | Fischer et al. |
| 2003/0208086 A1 | 11/2003 | Takahashi et al. |
| 2003/0216260 A1 | 11/2003 | Ruther et al. |
| 2004/0023959 A1 | 2/2004 | Fischer et al. |
| 2005/0054535 A1 | 3/2005 | Fischer et al. |
| 2005/0124247 A1 | 6/2005 | Billings |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0032539 A1 | 2/2007 | Himmler |
| 2007/0129252 A1 | 6/2007 | Fischer et al. |
| 2007/0225167 A1 | 9/2007 | Fischer et al. |
| 2007/0225170 A1 | 9/2007 | Fischer et al. |

(Continued)

FOREIGN PATENT DOCUMENTS

| | | |
|---|---|---|
| CA | 2 627 240 A1 | 5/2007 |
| DE | 1 993 9395 A1 | 4/2000 |

(Continued)

OTHER PUBLICATIONS

Ridley et al. (Pestic. Sci., 1998, v. 54, p. 327-337).*
Colby, S.R., "Calculating Synergistic and Antagonistic Responses of Herbicide Combinations," *Weeds* 15:20-22 (1967).
International Search Report for International Application No. PCT/EP2007/006133, European Patent Office, Netherlands, mailed on Jul. 3, 2008.
Dialog File 351, Derwent Patent Accession No. 13990789, English language abstract for JP 2003/201280 A (listed as FP37 on accompanying form PTO/SB/08A) (2003).
Co-pending, U.S. Appl. No. 12/373,205 inventors Fischer, R. et al., filed Nov. 30, 2009 (Not Published).
Co-pending, U.S. Appl. No. 12/373,648 inventors Fischer, R. et al., filed Dec. 4, 2009 (Not Published).
Co-pending, U.S. Appl. No. 12/373,197 inventors Fischer, R. et al., filed Nov. 12, 2009 (Not Published).
Co-pending, U.S. Appl. No. 12/373,188 inventors Fischer, R. et al., filed Oct. 16, 2009 (Not Published).

(Continued)

*Primary Examiner* — Robert Havlin
(74) *Attorney, Agent, or Firm* — Sterne, Kessler, Goldstein & Fox P.L.L.C.

(57) ABSTRACT

The new active compound combinations comprising compounds of the formula (I) and the active compounds (1) to (3) recited in the description possess very good insecticidal and/or acaricidal properties.

12 Claims, No Drawings

(56) References Cited

U.S. PATENT DOCUMENTS

| | | |
|---|---|---|
| 2007/0244007 A1 | 10/2007 | Fischer et al. |
| 2007/0254949 A1 | 11/2007 | Bretschneider et al. |
| 2007/0265266 A1 | 11/2007 | Fischer et al. |
| 2007/0270416 A1 | 11/2007 | Funke et al. |
| 2007/0275858 A1 | 11/2007 | Fischer et al. |
| 2007/0276023 A1 | 11/2007 | Fischer et al. |
| 2007/0298968 A1 | 12/2007 | Bretschneider et al. |
| 2007/0298969 A1 | 12/2007 | Fischer et al. |
| 2008/0027114 A1 | 1/2008 | Funke et al. |
| 2008/0167188 A1 | 7/2008 | Fischer et al. |
| 2008/0220973 A1 | 9/2008 | Fischer et al. |
| 2008/0287435 A1 | 11/2008 | Fischer et al. |
| 2008/0305955 A1 | 12/2008 | Bretschneider et al. |
| 2008/0318776 A1 | 12/2008 | Fischer et al. |
| 2009/0012100 A1 | 1/2009 | Fischer et al. |
| 2009/0012152 A1 | 1/2009 | Fischer et al. |
| 2009/0029858 A1 | 1/2009 | Fischer et al. |
| 2009/0215624 A1 | 8/2009 | Fischer et al. |
| 2009/0275471 A1* | 11/2009 | Funke et al. ............. 504/100 |
| 2009/0281157 A1 | 11/2009 | Fischer et al. |
| 2009/0298828 A1 | 12/2009 | Fischer et al. |
| 2010/0009850 A1 | 1/2010 | Fischer et al. |
| 2010/0048661 A1 | 2/2010 | Fischer et al. |
| 2010/0113437 A1 | 5/2010 | Fischer et al. |

FOREIGN PATENT DOCUMENTS

| | | |
|---|---|---|
| DE | 10 2005 051 325 A1 | 10/2005 |
| EP | 0 456 063 A2 | 11/1991 |
| EP | 0 521 334 A1 | 6/1992 |
| EP | 0 528 156 A1 | 2/1993 |
| EP | 0 596 298 A2 | 5/1994 |
| EP | 0 613 884 A2 | 9/1994 |
| EP | 0 613 885 A2 | 9/1994 |
| EP | 0 647 637 A1 | 4/1995 |
| EP | 0 668 267 A1 | 8/1995 |
| JP | 2003/201280 A | 7/2003 |
| WO | WO 95/01971 A1 | 1/1995 |
| WO | WO 95/20572 A1 | 8/1995 |
| WO | WO 95/26345 A1 | 10/1995 |
| WO | WO 95/26954 A1 | 10/1995 |
| WO | WO 96/20196 A1 | 7/1996 |
| WO | WO 96/25395 A1 | 8/1996 |
| WO | WO 96/35664 A1 | 11/1996 |
| WO | WO 97/01535 A1 | 1/1997 |
| WO | WO 97/02243 A1 | 1/1997 |
| WO | WO 97/36868 A1 | 10/1997 |
| WO | WO 97/43275 A2 | 11/1997 |
| WO | WO 98/05638 A2 | 2/1998 |
| WO | WO 98/06721 A1 | 2/1998 |
| WO | WO 98/25928 A1 | 6/1998 |
| WO | WO 98/35935 A1 | 8/1998 |
| WO | WO 99/16748 A1 | 4/1999 |
| WO | WO 99/24437 A1 | 5/1999 |
| WO | WO 99/43649 A1 | 9/1999 |
| WO | WO 99/48869 A1 | 9/1999 |
| WO | WO 99/55673 A1 | 11/1999 |
| WO | WO 00/42850 A1 | 7/2000 |
| WO | WO 01/17972 A2 | 3/2001 |
| WO | WO 01/23354 A2 | 4/2001 |
| WO | WO 01/33966 A2 | 5/2001 |
| WO | WO 01/74770 A1 | 10/2001 |
| WO | WO 02/14263 A1 | 2/2002 |
| WO | WO 02/37963 A1 | 5/2002 |
| WO | WO 03/013249 A1 | 2/2003 |
| WO | WO 2004/007448 A1 | 1/2004 |
| WO | WO 2004/024688 A1 | 3/2004 |
| WO | WO 2004/065366 A1 | 8/2004 |
| WO | WO 2004/080962 A1 | 9/2004 |
| WO | WO 2004/111042 A1 | 12/2004 |
| WO | WO 2005/044791 A2 | 5/2005 |
| WO | WO 2005/044796 A1 | 5/2005 |
| WO | WO 2005/048710 A1 | 6/2005 |
| WO | WO 2005/049569 A1 | 6/2005 |
| WO | WO 2005/066125 A1 | 7/2005 |
| WO | WO 2005/092897 A2 | 10/2005 |
| WO | WO 2006/000355 A1 | 1/2006 |
| WO | WO 2006/002824 A1 | 1/2006 |
| WO | WO 2006/029799 A1 | 3/2006 |
| WO | WO 2006/056281 A1 | 6/2006 |
| WO | WO 2006/056282 A1 | 6/2006 |
| WO | WO 2006/077071 A2 | 6/2006 |
| WO | WO 2006/089633 A2 | 8/2006 |
| WO | WO 2006128863 * | 12/2006 | ............. A01N 37/52 |
| WO | WO 2007009661 * | 1/2007 | |
| WO | WO 2007017433 * | 2/2007 | ............. A01N 43/56 |
| WO | WO 2007079162 * | 7/2007 | ........... C07D 261/04 |
| ZA | 99/6662 | 10/1999 |
| ZA | 9906662 | 10/2000 |

OTHER PUBLICATIONS

Co-pending, U.S. Appl. No. 12/517,419 inventors Bretschneider, T. et al., filed Dec. 15, 2009 (Not Published).

Co-pending, U.S. Appl. No. 12/517,179 inventors Fischer, R. et al., filed Nov. 24, 2009 (Not Published).

Co-pending, U.S. Appl. No. 12/598,932 inventors Fischer, R. et al., filed May 9, 2008 (Not Published).

Co-pending, U.S. Appl. No. 12/591,267 inventors Fischer, R. et al., filed Nov. 13, 2009 (Not Published).

Co-pending, U.S. Appl. No. 12/591,456 inventors Fischer, R. et al., filed Nov. 19, 2009 (Not Published).

Co-pending, U.S. Appl. No. 12/665,674 inventors Fischer, R. et al., filed May 25, 2010 (Not Published).

Co-pending, U.S. Appl. No. 12/666,834 inventors Fischer, R. et al., filed Jun. 4, 2010 (Not Published).

English language translation (unverified machine translation) of Japanese Patent Publication No. JP 2003/201280 A, Japanese Patent Office, Patent & Utility Model Gazette DB, Patent Abstract of Japan, 2003.

Bauer, T.A., et al., "Response of Selected Weed Species to Postemergence Imazethapyr and Bentazon," Weed Tech. 9:236-242, The Weed Science Society of America (1995).

Blackshaw, R.E., "HOE-39866 Use in Chemical Fallow Systems," Weed Tech. 3:420-428, The Weed Science Society of America (1989).

Blackshaw, R.E., "Synergistic Mixes of DPX-A7881 and Clopyralid in Canola (Brassica napus)," Weed Tech. 3:690-695, The Weed Science Society of America (1989).

Blackshaw, R.E., et al., "Herbicide Combinations for Postemergent Weed Control in Safflower (Carthamus tinctorius)," Weed Tech. 4:97-104, The Weed Science Society of America (1990).

Blouin, D.C., et al., "Analysis of Synergistic and Antagonistic Effects of Herbicides Using Nonlinear Mixed-Model Methodology," Weed Tech. 18:464-472, The Weed Science Society of America (2004).

Bradley, P.R., et al., "Response of Sorghum (Sorghum bicolor) to Atrazine, Ammonium Sulfate, and Glyphosate," Weed Tech. 14:15-18, The Weed Science Society of America (2000).

Buker, III, R.S., et al., "Confirmation and Control of a Paraquat-Tolerant Goosegrass (Eleusine indica) Biotype," Weed Tech. 16:309-313, The Weed Science Society of America (2002).

Burke, I.C., et al., "CGA-362622 Antagonizes Annual Grass Control with Clethodim," Weed Tech. 16:749-754, The Weed Science Society of America (2002).

Flint, J.L., et al., "Analyzing Herbicide Interactions, A Statistical Treatment of Colby's Method," Weed Tech. 2:304-309, The Weed Science Society of America (1988).

Gillespie, G.R., and Nalewaja, J.D., "Wheat (Triticum aestivum) Response to Triallate Plus Chlorsulfuron," Weed Tech. 3:20-23, The Weed Science Society of America (1989).

Green, J.M., et al., "Metribuzin and Chlorimuron Mixtures for Preemergence Broadleaf Weed Control in Soybeans, Glycine max," Weed Tech. 2:355-363, The Weed Science Society of America (1988).

Harker, K.N., and O'Sullivan, P.A., "Synergistic Mixtures of Sethoxydim and Fluazifop on Annual Grass Weeds," Weed Tech. 5:310-316, The Weed Science Society of America (1991).

Kent, L.M., et al., "Effect of Ammonium Sulfate, Imazapyr, and Environment on the Phytotoxicity of Imazethapyr," Weed Tech. 5:202-205, The Weed Science Society of America (1991).

(56) References Cited

OTHER PUBLICATIONS

Kotoula-Syka, E., et al., "Interactions between SAN 582H and Selected Safeners on Grain *Sorghum* (*Sorghum bicolor*) and Corn (*Zea mays*)," *Weed Tech. 10*:299-304, The Weed Science Society of America (1996).

Lanclos, D.Y., et al., "Glufosinate Tank-Mix Combinations in Glufosinate-Resistant Rice (*Oryza sativa*)," *Weed Tech. 16*:659-663, The Weed Science Society of America (2002).

Norris, J.L., et al., "Weed Control from Herbicide Combinations with Three Formulations of Glyphosate," *Weed Tech. 15*:552-558, The Weed Science Society of America (2001).

Novosel, K.M., et al., "Metolachlor Efficacy as Influenced by Three Acetolactate Synthase-Inhibiting Herbicides," *Weed Tech. 12*:248-253, The Weed Science Society of America (1998).

Palmer, E.W., et al., "Broadleaf Weed Control in Soybean (*Glycine max*) with CGA-277476 and Four Postemergence Herbicides," *Weed Tech. 14*:617-623, The Weed Science Society of America (2000).

Rummens, F.H.A., "An Improved Definition of Synergistic and Antagonistic Effects," *Weed Science 23*(1):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech. 6*:922-929, The Weed Science Society of America (1992).

Scott, R.C., et al., "Spray Adjuvant, Formulation, and Environmental Effects on Synergism and Post-Applied Tank Mixtures of SAN 582H with Fluazifop-P, Imazethapyr, and Sethoxydim," *Weed Tech. 12*:463-469, The Weed Science Society of America (1998).

Shaw, D.R. and Arnold, J.C., "Weed Control from Herbicide Combinations with Glyphosate," *Weed Tech. 16*:1-6, The Weed Science Society of America (2002).

Snipes, C.E., and Allen, R.L., "Interaction of Graminicides Applied in Combination with Pyrithiobac," *Weed Tech. 10*:889-892, The Weed Science Society of America (1996).

Sun, Y.-P. & Johnson, E.R., "Analysis of Joint Action of Insecticides Against House Flies", *J. Econ. Entomol. 53*:887-892, United States (1960).

Tammes, P.M.L., "Isoboles, A Graphic Representation of Synergism in Pesticides," *Neth. J. Plant Path. 70*:73-80, Springer, Germany (1964).

Wehtje, G. and Walker, R.H., "Interaction of Glyphosate and 2,4-DB for the Control of Selected Morningglory (*Ipomoea* spp.) Species," *Weed Tech. 11*:152-156, The Weed Science Society of America (1997).

Zhang, W., et al., "Fenoxaprop Interactions for Barnyardgrass (*Echinochloa crus-galli*) Control in Rice," *Weed Tech. 19*:293-297, The Weed Science Society of America (2005).

Office Action mailed Jun. 13, 2011, in U.S. Appl. No. 11/572,400, Fischer et al., § 371(c) date Jul. 22, 2008.

Office Action, mailed Jun. 13, 2011, in U.S. Appl. No. 11/572,400, Fischer et al., filed Jul. 22, 2008.

\* cited by examiner

ACTIVE INGREDIENT COMBINATIONS HAVING INSECTICIDE AND ACARICIDE PROPERTIES

The present invention relates to new active compound combinations which are composed of known cyclic keto enols on the one hand and of further known active insecticidal compounds on the other hand and which are highly suitable for controlling animal pests such as insects and/or unwanted acarids.

It is already known that certain cyclic keto enols possess herbicidal and/or insecticidal and/or acaricidal properties. At low application rates, the activity of these compounds, though good, is unsatisfactory in certain cases.

Known compounds having a herbicidal and/or insecticidal and/or acaricidal action are 1H-3-arylpyrrolidine-2,4-dione derivatives (EP-A-456 063, EP-A-521 334, EP-A-596 298, EP-A-613 884, EP-A-613 885, WO 95/01997, WO 95/26954, WO 95/20572, EP-A-0 668 267, WO 96/25395, WO 96/35664, WO 97/01535, WO 97/02243, WO 97/36868, WO 97/43275, WO 98/05638, WO 98/06721, WO 98/25928, WO 99/16748, WO 99/24437, WO 99/43649, WO 99/48869, WO 99/55673, WO 01/17972, WO 01/23354, WO 01/74770, WO 03/013249, WO 04/007448, WO 04/024688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633 and DE-A-05051325, WO 06/077071).

Also known are 3-aryl-Δ³-dihydrofuranone derivatives having herbicidal, acaricidal and insecticidal properties, from EP-A-528 156, EP-A-0 647 637, WO 95/26345, WO 96/20196, WO 96/25395, WO 96/35664, WO 97/01535, WO 97/02243, WO 97/36868, WO 98/05638, WO 98/25928, WO 99/16748, WO 99/43649, WO 99/48869, WO 99/55673, WO 00/42850, WO 01/17972, WO 01/23354, WO 01/74770, WO 03/013249, WO 04/024688, WO 04/080962, WO 04/111042, WO 05/092897, WO 06/000355, WO 06/002824 and WO 06/029799.

It has now been found that active compound combinations comprising compounds of the formula (I)

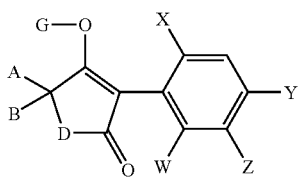

(I)

in which

X represents halogen, alkyl, alkoxy, haloalkyl, haloalkoxy or cyano,

W, Y and Z independently of one another represent hydrogen, halogen, alkyl, alkoxy, haloalkyl, haloalkoxy or cyano, A represents hydrogen, in each case optionally halogen-substituted alkyl or alkoxyalkyl, or saturated, optionally substituted cycloalkyl in which optionally at least one ring atom has been replaced by a heteroatom, B represents hydrogen or alkyl, or A and B, together with the carbon atom to which they are attached, represent a saturated or unsaturated, unsubstituted or substituted cyclic moiety which optionally contains at least one heteroatom, D represents NH or oxygen, G represents hydrogen (a) or represents one of the groups

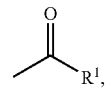
(b)

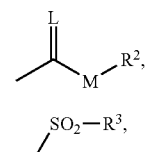
(c)

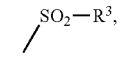
(d)

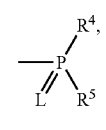
(e)

E or
(f)

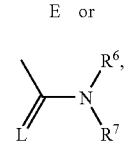
(g)

in which

E represents a metal ion or an ammonium ion,

L represents oxygen or sulphur,

M represents oxygen or sulphur,

R¹ represents in each case optionally halogen-substituted alkyl, alkenyl, alkoxyalkyl, alkylthioalkyl or polyalkoxyalkyl or optionally halogen-, alkyl- or alkoxy-substituted cycloalkyl, which may be interrupted by at least one heteroatom, or in each case optionally substituted phenyl, phenylalkyl, hetaryl, phenoxyalkyl or hetaryloxyalkyl, R² represents in each case optionally halogen-substituted alkyl, alkenyl, alkoxyalkyl or polyalkoxyalkyl or represents in each case optionally substituted cycloalkyl, phenyl or benzyl, R³ represents optionally halogen-substituted alkyl or optionally substituted phenyl, R⁴ and R⁵ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio and R⁶ and R⁷ independently of one another represent hydrogen, in each case optionally halogen-substituted alkyl, cycloalkyl, alkenyl, alkoxy or alkoxyalkyl, represent optionally substituted phenyl, represent optionally substituted benzyl or, together with the N atom to which they are attached, represent an optionally substituted ring which is optionally interrupted by oxygen or sulphur in the form of their isomer mixtures or pure isomers and 1. cyenopyrafen (1E)-2-cyano-2-[4-(1,1-dimethylethyl)phenyl]-1-(1,3,4-trimethyl-1H-pyrazol-5-yl)ethenyl 2,2-dimethylpropanoate

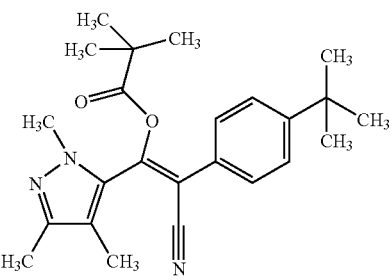 [SMILES: Cc1nn(C)c(/C(OC(=O)C(C)(C)C)=C(\C#N)c2ccc(C(C)(C)C)cc2)c1C]

known from JP 2003 201 280
and/or 2. cyflumetofen 2-methoxyethyl alpha-cyano-alpha-[4-(1,1-dimethylethyl)phenyl]-beta-oxo-2-(trifluoromethyl)benzenepropanoate

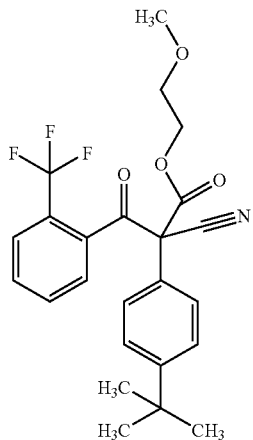 [SMILES: COCCOC(=O)C(C#N)(C(=O)c1ccccc1C(F)(F)F)c1ccc(C(C)(C)C)cc1]

known from WO 2002/014263
and/or

3. IKA 2002

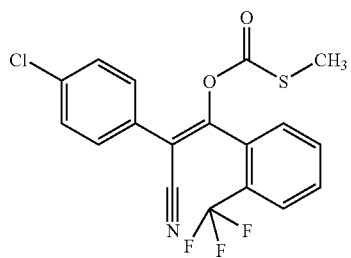 [SMILES: CSC(=O)O/C(=C(/C#N)c1ccc(Cl)cc1)c1ccccc1C(F)(F)F]

known from WO 98/35935 possess very good insecticidal and/or acaricidal properties.

With preference it is possible to employ active compound combinations comprising compounds of the abovementioned formula (I) in which the radicals have the following definition:

W preferably represents hydrogen, $C_1$-$C_4$-alkyl, $C_1$-$C_4$-alkoxy, chloro, bromo or fluoro, X preferably represents $C_1$-$C_4$-alkyl, $C_1$-$C_4$-alkoxy, $C_1$-$C_4$-haloalkyl, fluoro, chloro or bromo, Y and Z independently of one another preferably represent hydrogen, $C_1$-$C_4$-alkyl, halogen, $C_1$-$C_4$-alkoxy or $C_1$-$C_4$-haloalkyl, A preferably represents hydrogen or in each case optionally halogen-substituted $C_1$-$C_6$-alkyl or $C_3$-$C_8$-cycloalkyl, B preferably represents hydrogen, methyl or ethyl, A, B and the carbon atom to which they are attached preferably represent saturated $C_3$-$C_6$-cycloalkyl in which optionally one ring member has been replaced by oxygen or sulphur and which is optionally substituted once or twice by $C_1$-$C_4$-alkyl, trifluoromethyl or $C_1$-$C_4$-alkoxy, D preferably represents NH or oxygen, G preferably represents hydrogen (a) or represents one of the groups (b)

(c)

(d)

(e)

E, or (f)

(g)

more particularly representing (a), (b), (c), or (g)
in which
E represents a metal ion or an ammonium ion,
L represents oxygen or sulphur and
M represents oxygen or sulphur, $R^1$ preferably represents in each case optionally halogen-substituted $C_1$-$C_{10}$-alkyl, $C_2$-$C_{10}$-alkenyl, $C_1$-$C_4$-alkoxy-$C_1$-$C_4$-alkyl or $C_1$-$C_4$-alkylthio-$C_1$-$C_4$-alkyl or optionally fluoro-, chloro-, $C_1$-$C_4$-alkyl- or $C_1$-$C_2$-alkoxy-substituted $C_3$-$C_6$-cycloalkyl, represents optionally fluoro-, chloro-, bromo-, cyano-, nitro-, $C_1$-$C_4$-alkyl, $C_1$-$C_4$-alkoxy, trifluoromethyl- or trifluoromethoxy-substituted phenyl, represents thienyl or pyridyl in each case optionally substituted by chloro or methyl, $R^2$ preferably represents in each case optionally fluoro- or chloro-substituted $C_1$-$C_{10}$-alkyl, $C_2$-$C_{10}$-alkenyl or $C_1$-$C_4$-alkoxy-$C_2$-$C_4$-alkyl, represents optionally methyl- or methoxy-substituted $C_5$-$C_6$-cycloalkyl or represents in each case optionally fluoro-, chloro-, bromo-, cyano-, nitro-, $C_1$-$C_4$-alkyl-, $C_1$-$C_4$-alkoxy-, trifluoromethyl- or trifluoromethoxy-substituted phenyl or benzyl, $R^3$ preferably represents optionally fluoro-substituted $C_1$-$C_4$-alkyl or represents optionally fluoro-, chloro-, bromo-, $C_1$-$C_4$-alkyl-, $C_1$-$C_4$-alkoxy-, trifluoromethyl-, trifluoromethoxy-, cyano- or nitro-substituted phenyl, $R^4$ preferably represents in each case optionally fluoro- or chloro-substituted $C_1$-$C_4$-alkyl, $C_1$-$C_4$-alkoxy, $C_1$-$C_4$-alkylamino or $C_1$-$C_4$-alkylthio or represents in each case optionally fluoro-, chloro-, bromo-, nitro-, cyano-, $C_1$-$C_4$-alkoxy-, trifluoromethoxy-, $C_1$-$C_4$-alkylthio-, $C_1$-$C_4$-haloalkylthio-, $C_1$-$C_4$-alkyl- or trifluoromethyl-substituted phenyl, phenoxy or phenylthio, $R^5$ preferably represents $C_1$-$C_4$-alkoxy or $C_1$-$C_4$-thioalkyl, $R^6$ preferably represents $C_1$-$C_6$-alkyl, $C_3$-$C_6$-cycloalkyl, $C_1$-$C_6$-alkoxy, $C_3$-$C_6$-alkenyl or $C_1$-$C_4$-alkoxy-$C_1$-$C_4$-alkyl, $R^7$ preferably represents $C_1$-$C_6$-alkyl, $C_3$-$C_6$-alkenyl or $C_1$-$C_4$-alkoxy-$C_1$-$C_4$-alkyl, $R^6$ and $R^7$ together preferably represent an optionally methyl- or ethyl-substituted $C_3$-$C_6$-alkylene radical in which optionally one carbon atom has been replaced by oxygen or sulphur in the form of their isomer mixtures or pure isomers.

With particular preference it is possible to employ active compound combinations comprising compounds of the abovementioned formula (I) in which the radicals have the following definition:

W with particular preference represents hydrogen, methyl, ethyl, chloro, bromo or methoxy, X with particular preference represents chloro, bromo, methyl, ethyl, propyl, isopropyl, methoxy, ethoxy or trifluoromethyl, Y and Z with particular preference independently of one another represent hydrogen, fluoro, chloro, bromo, methyl, ethyl, propyl, isopropyl, trifluoromethyl or methoxy, A with particular preference represents methyl, ethyl, propyl, isopropyl, butyl, isobutyl, sec-butyl, tert-butyl, cyclopropyl, cyclopentyl or cyclohexyl, B with particular preference represents hydrogen, methyl or ethyl, or A, B and the carbon atom to which they are attached with particular preference represent saturated $C_5$-$C_6$-cycloalkyl in which optionally one ring member has been replaced by oxygen and which is optionally substituted once by methyl, ethyl, trifluoromethyl, methoxy, ethoxy, propoxy or butoxy, D with particular preference represents NH or oxygen, G with particular preference represents hydrogen (a) or represents one of the groups

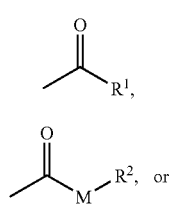

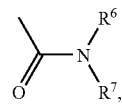

in which

M represents oxygen or sulphur, $R^1$ with particular preference represents $C_1$-$C_8$-alkyl, $C_2$-$C_4$-alkenyl, methoxymethyl, ethoxymethyl, ethylthiomethyl, cyclopropyl, cyclopentyl or cyclohexyl, represents phenyl which is optionally substituted once or twice by fluoro, chloro, bromo, cyano, nitro, methyl, ethyl, methoxy, trifluoromethyl or trifluoromethoxy, represents thienyl or pyridyl in each case optionally substituted by chloro or methyl, $R^2$ with particular preference represents $C_1$-$C_8$-alkyl, $C_2$-$C_4$-alkenyl, methoxyethyl or ethoxyethyl or represents phenyl or benzyl, $R^6$ and $R^7$ independently of one another with particular preference represent methyl or ethyl or together represent a $C_5$-alkylene radical in which the $C_3$ methylene group has been replaced by oxygen in the form of their isomer mixtures or pure isomers.

With very particular preference it is possible to employ active compound combinations comprising compounds of the abovementioned formula (I) in which the radicals have the following definition:

W with very particular preference represents hydrogen or methyl,

X with very particular preference represents chloro, bromo or methyl,

Y and Z with very particular preference independently of one another represent hydrogen, chloro, bromo or methyl, A, B and the carbon atom to which they are attached with very particular preference represent saturated $C_5$-$C_6$-cycloalkyl in which optionally one ring member has been replaced by oxygen and which is optionally substituted once by methyl, trifluoromethyl, methoxy, ethoxy, propoxy or butoxy, D with very particular preference represents NH or oxygen, G with very particular preference represents hydrogen (a) or represents one of the groups

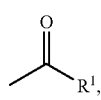

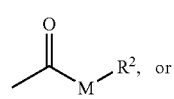

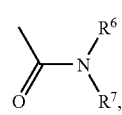

in which

M represents oxygen or sulphur, $R^1$ with very particular preference represents $C_1$-$C_8$-alkyl, $C_2$-$C_4$-alkenyl, methoxy-methyl, ethoxymethyl, ethylthiomethyl, cyclopropyl, cyclopentyl or cyclohexyl or represents phenyl which is optionally substituted once by fluoro, chloro, bromo, methyl, methoxy, trifluoromethyl, trifluoromethoxy, cyano or nitro, represents thienyl or pyridyl in each case optionally substituted by chloro or methyl, $R^2$ with very particular preference represents $C_1$-$C_8$-alkyl, $C_2$-$C_4$-alkenyl, methoxyethyl, ethoxyethyl, phenyl or benzyl, $R^6$ and $R^7$ independently of one another with very particular preference represent methyl or ethyl or together represent a $C_5$-alkylene radical in which the $C_3$ methylene group has been replaced by oxygen in the form of their isomer mixtures or pure isomers.

With a special preference it is possible to employ active compound combinations comprising compounds of the formula (I) from the following patents/patent applications, cited on page 1, in which the radicals A, B, D, G, W, X, Y, Z, $R^1$, $R^2$, $R^6$ and $R^7$ have the definitions stated in the very particularly preferred ranges: EP-A-528 156, WO 97/01535, WO 97/36868, WO 98/05638, WO 04/007448.

Highlighted from these applications, the following compounds of the formula (I)

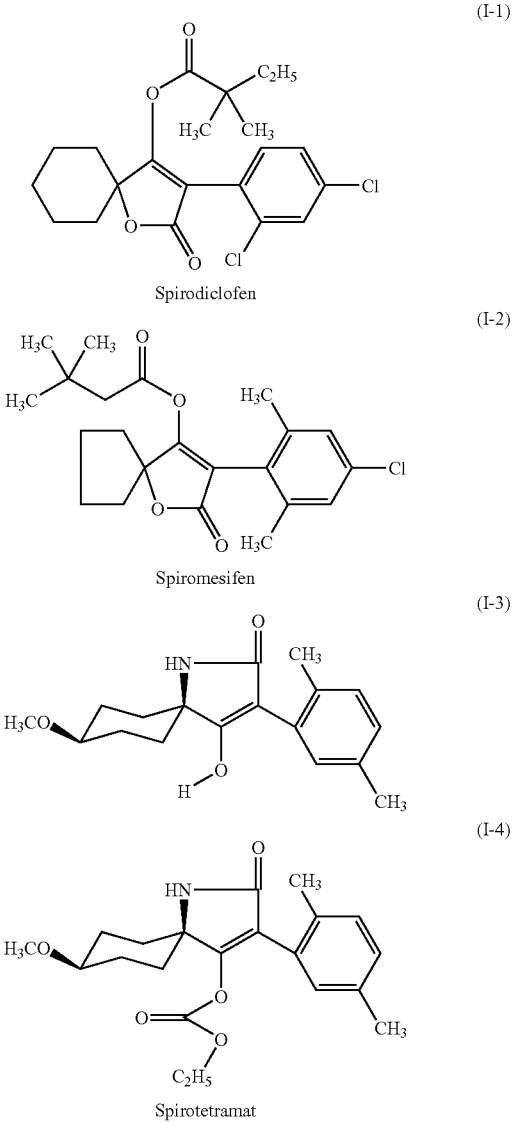

Spirodiclofen (I-1)

Spiromesifen (I-2)

(I-3)

Spirotetramat (I-4)

can be employed for active compound combinations with compounds 1 to 3.

The insecticidal and/or acaricidal action of the active compound combinations of the invention is, surprisingly, substantially higher than the sum of the actions of the individual active compounds. The unforeseeable effect is a true synergistic effect and not merely a complementarity of action.

As well as at least one active compound of the formula (I), the active compound combinations of the invention comprise at least one active compound 1 to 3.

When the active compounds are present in the active compound combinations of the invention in certain proportions by weight, the synergistic effect is particularly marked. However, the weight ratios of the active compounds in the active compound combinations can be varied within a relatively broad range. Generally speaking, the combinations according to the invention comprise active compounds of the formula (I) and the co-components in the preferred, particularly preferred and very particularly preferred proportions indicated in the tables which now follow:

| Co-component | Preferred ratio | Particularly preferred ratio | Very particularly preferred ratio |
|---|---|---|---|
| Spirodiclofen (I-1) | 25:1 to 1:25 | 10:1 to 1:10 | 5:1 to 1:5 |
| Spiromesifen (I-2) | 25:1 to 1:25 | 10:1 to 1:10 | 5:1 to 1:5 |
| (I-3) | 25:1 to 1:25 | 10:1 to 1:10 | 5:1 to 1:5 |
| Spirotetramat (I-4) | 25:1 to 1:25 | 10:1 to 1:10 | 5:1 to 1:5 |

* The proportions are based on weight ratios. The ratio is to be understood as active compound of the formula (I):cyenopyrafen (1.)

| Co-component | Preferred ratio | Particularly preferred ratio | Very particularly preferred ratio |
|---|---|---|---|
| Spirodiclofen (I-1) | 25:1 to 1:25 | 10:1 to 1:10 | 5:1 to 1:5 |
| Spiromesifen (I-2) | 25:1 to 1:25 | 10:1 to 1:10 | 5:1 to 1:5 |
| (I-3) | 25:1 to 1:25 | 10:1 to 1:10 | 5:1 to 1:5 |
| Spirotetramat (I-4) | 25:1 to 1:25 | 10:1 to 1:10 | 5:1 to 1:5 |

* the proportions are based on weight ratios. The ratio is to be understood as active compound of the formula (I):cyflumetofen (2.)

| Co-component | Preferred ratio | Particularly preferred ratio | Very particularly preferred ratio |
|---|---|---|---|
| Spirodiclofen (I-1) | 25:1 to 1:25 | 10:1 to 1:10 | 5:1 to 1:5 |
| Spiromesifen (I-2) | 25:1 to 1:25 | 10:1 to 1:10 | 5:1 to 1:5 |
| (I-3) | 25:1 to 1:25 | 10:1 to 1:10 | 5:1 to 1:5 |
| Spirotetramat (I-4) | 25:1 to 1:25 | 10:1 to 1:10 | 5:1 to 1:5 |

* the proportions are based on weight ratios. The ratio is to be understood as active compound of the formula (I):IKA 2002 (3.)

In addition, the active compound combinations may also comprise further fungicidally, acaricidally or insecticidally active admix components.

The active compound combinations according to the invention are suitable for controlling animal pests, preferably arthropods and nematodes, more particularly insects and/or arachnids, found in vine growing, fruit growing, horticulture, agriculture, in animal health, in forests, in the protection of stored products and materials and in the hygiene sector. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus, Gryllotalpa* spp., *Locusta migratoria migratorioides, Melanoplus* spp., *Schistocerca gregaria*.

From the order of the Blattaria, for example, *Blatta orientalis, Periplaneta americana, Leucophaea maderae, Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis*.

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera ni, Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus*.

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:
for example ammonium salts and ground natural minerals such as kaolins, clays, talc, chalk, quartz, attapulgite, montmorillonite or diatomaceous earth, and ground synthetic materials such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, head lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally etc.), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10 000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:
Beetles such as
*Hylotrupes bajulus, Chlorophorus pilosis, Anobium punctatum, Xestobium rufovillosum, Ptilinus pecticornis, Dendro-*

*bium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenoptera such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristle-tails such as *Lepisma saccharina.*

Industrial materials in the present context are understood as meaning non-living materials such as, preferably, polymers, adhesives, glues, paper and board, leather, wood, timber products and paints.

The material which is to be protected from insect attack is very particularly preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellent, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

According to a preferred embodiment, some of the organochemical solvent or solvent mixture or an aliphatic polar organochemical solvent or solvent mixture is replaced. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellents, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl) adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can equally be employed for protecting objects which come into contact with seawater or brackish water, such as hulls, screens, nets, buildings, quaysides and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent stops in the dry dock.

Apart from fouling by algae, for example *Ectocarpus* sp. and *Ceramium* sp., fouling by sessile Entomostraka groups, which come under the name Cirripedia (cirriped crustaceans), is of particular importance.

Surprisingly, it has now been found that the active compound combinations according to the invention have an outstanding antifouling action.

Use of the active compound combinations according to the invention allows the use of heavy metals such as, for example, in bis(trialkyltin) sulphides, tri-n-butyltin laurate, tri-n-butyltin chloride, copper(I) oxide, triethyltin chloride, tri-n-butyl (2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferable suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propynyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacrb;
or conventional antifouling active compounds such as
4,5-dichloro-2-octyl-4-isothiazolin-3-one, diiodomethylparatryl sulphone, 2-(N,N-dimethyl-thiocarbamoylthio)-5-nitrothiazyl, potassium salts, copper salts, sodium salts and zinc salts of 2-pyridinethiol 1-oxide, pyridine-triphenylborane, tetrabutyldistannoxane, 2,3,5,6-tetra-chloro-4-(methylsulphonyl)pyridine, 2,4,5,6-tetrachloroisophthalonitrile, tetramethylthiuram disulphide and 2,4,6-trichlorophenylmaleimide.

The antifouling compositions used comprise the active compound combinations according to the invention in a concentration of 0.001 to 50% by weight, in particular 0.01 to 20% by weight.

Moreover, the antifouling compositions according to the invention comprise the customary constituents such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in seawater. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais*, *Stegobium paniceum*.

From the order of the Diptera, for example, *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga carnaria*, *Simulium* spp., *Stomoxys calcitrans*, *Tipula paludosa*.

From the order of the Lepidoptera, for example, *Achroia grisella*, *Galleria mellonella*, *Plodia interpunctella*, *Tinea cloacella*, *Tinea pellionella*, *Tineola bisselliella*.

From the order of the Siphonaptera, for example, *Ctenocephalides canis*, *Ctenocephalides felis*, *Pulex irritans*, *Tunga penetrans*, *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp., *Tetramorium caespitum*.

From the order of the Anoplura, for example, *Pediculus humanus capitis*, *Pediculus humanus corporis*, *Phthirus pubis*.

From the order of the Heteroptera, for example, *Cimex hemipterus*, *Cimex lectularius*, *Rhodnius prolixus*, *Triatoma infestans*.

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are particularly emphasized are the increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) in the plants (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes in question which impart the desired traits can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plants will be developed and/or marketed in the future.

The plants listed can be treated according to the invention in a particularly advantageous manner with the active compound mixtures according to the invention. The preferred ranges stated above for the mixtures also apply to the treatment of these plants. Particular emphasis is given to the treatment of plants with the mixtures specifically mentioned in the present text.

The good insecticidal and acaricidal action of the active compound combinations according to the invention can be seen from the examples which follow. While the individual active compounds show weaknesses in their action, the combinations show an action which exceeds a simple summation of actions.

A synergistic effect in insecticides and acaricides is always present when the action of the active compound combinations exceeds the total of the actions of the active compounds when applied individually.

The action to be expected for a given combination of two active compounds can be calculated as follows in accordance with S. R. Colby, Weeds 15 (1967), 20-22:

If

X is the kill rate, expressed in % of the untreated control, when employing active compound A at an application rate of m g/ha or in a concentration of m ppm, Y is the kill rate, expressed in % of the untreated control, when employing active compound B at an application rate of n g/ha or in a concentration of n ppm and E is the kill rate, expressed in % of the untreated control, when employing active compounds A and B at application rates of m and n g/ha or in a concentration of m and n ppm, then $$E = X + Y - \frac{X \cdot Y}{100}$$

If the actual insecticidal kill rate exceeds the calculated value, the killing action of the combination is superadditive, i.e. a synergistic effect is present. In this case, the kill rate actually observed must exceed the value calculated using the above formula for the expected kill rate (E).

After the desired time a determination is made of the kill level in %. 100% here means that all of the animals have been killed; 0% means that no animals have been killed.

EXAMPLE A

Myzus persicae Test

Solvents: 78 parts by weight of acetone
   1.5 parts by weight of dimethylformamide
Emulsifier: 0.5 part by weight of alkylaryl polyglycol ether An appropriate preparation of active compound is prepared by mixing 1 part by weight of active compound with the stated amounts of solvents and emulsifier and diluting the concentrate with emulsifier-containing water to the desired concentration.

Cabbage leaves (*Brassica oleracea*) heavily infested by the green peach aphid (*Myzus persicae*) are treated by spraying with the active compound preparation at the desired concentration.

After the desired time has elapsed a determination is made of the kill level in %. 100% here means that all of the aphids have been killed; 0% means that no aphids have been killed. The kill rates found are calculated by the Colby formula.

In this test a synergistically boosted activity as compared with the active compounds applied individually is found for the following active compound combination in accordance with the present application:

TABLE A

Phytopathogenic insects
*Myzus persicae* test

| Active compound | Concentration in g/ha | Kill level in % after 6$^d$ | |
|---|---|---|---|
| Cyenopyrafen | 100 | 0 | |
| Cyflumetofen | 100 | 0 | |
| Spiromesifen | 100 | 70 | |
| Cyenopyrafen + Spiromesifen (1:1) | | | |
| inventive | | found* | calc.** |
| | 100 + 100 | 80 | 70 |
| Cyflumetofen + Spiromesifen (1:1) | | | |
| inventive | | found* | calc.** |
| | 100 + 100 | 90 | 70 |

*found = action found
**calc. = action calculated by the Colby formula

EXAMPLE B

Phaedon cochleariae Larvae Test

Solvents: 78 parts by weight of acetone
   1.5 parts by weight of dimethylformamide
Emulsifier: 0.5 part by weight of alkylaryl polyglycol ether An appropriate preparation of active compound is prepared by mixing 1 part by weight of active compound with the stated amounts of solvents and emulsifier and diluting the concentrate with emulsifier-containing water to the desired concentration.

Cabbage leaves (*Brassica oleracea*) are treated by spraying with the active compound preparation at the desired concentration and are populated with larvae of the mustard beetle (*Phaedon cochleariae*) while the leaves are still moist.

After the desired time has elapsed a determination is made of the kill level in %. 100% here means that all of the beetle larvae have been killed; 0% means that no beetle larvae have been killed. The kill rates found are calculated by the Colby formula.

In this test a synergistically boosted activity as compared with the active compounds applied individually is found for the following active compound combination in accordance with the present application:

TABLE B

Phytopathogenic insects
*Phaedon cochleariae* larvae test

| Active compound | Concentration in g/ha | Kill level in % after $6^d$ |
|---|---|---|
| Cyenopyrafen | 100 | 50 |
| Cyflumetofen | 100 | 0 |
| IKA 2002 | 100 | 33 |
| Spirotetramat | 100 | 33 |
| Cyenopyrafen + Spirotetramat (1:1) | | |
| inventive | found* | calc.** |
| | 100 + 100 | 100 55.11 |
| Cyflumetofen + Spirotetramat (1:1) | | |
| inventive | found* | calc.** |
| | 100 + 100 | 83 33 |
| IKA 2002 + Spirotetramat (1:1) | | |
| inventive | found* | calc.** |
| | 100 + 100 | 100 66.5 |

*found = action found
**calc. = action calculated by the Colby formula

EXAMPLE C

*Spodoptera frugiperda* Test

Solvents: 78 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvents and emulsifier and diluting the concentrate with emulsifier-containing water to the desired concentration.

Cabbage leaves (*Brassica oleracea*) are treated by spraying with the active compound preparation at the desired concentration and are populated with larvae of the army worm (*Spodoptera frugiperda*) while the leaves are still moist.

After the desired time has elapsed a determination is made of the kill level in %. 100% here means that all of the caterpillars have been killed; 0% means that no caterpillars have been killed. The kill rates found are calculated by the Colby formula.

In this test a synergistically boosted activity as compared with the active compounds applied individually is found for the following active compound combination in accordance with the present application:

TABLE C

Phytopathogenic insects
*Spodoptera frugiperda* test

| Active compound | Concentration in g/ha | Kill level in % after $6^d$ |
|---|---|---|
| Cyflumetofen | 100 | 0 |
| IKA 2002 | 100 | 0 |
| Spirotetramat | 100 | 50 |

TABLE C-continued

Phytopathogenic insects
*Spodoptera frugiperda* test

| Active compound | Concentration in g/ha | Kill level in % after $6^d$ |
|---|---|---|
| Cyflumetofen + Spirotetramat (1:1) | | |
| inventive | found* | calc.** |
| | 100 + 100 | 100 50 |
| IKA 2002 + Spirotetramat (1:1) | | |
| inventive | found* | calc.** |
| | 100 + 100 | 83 50 |

*found = action found
**calc. = action calculated by the Colby formula

EXAMPLE D

*Tetranychus urticae* Test

Solvents: 78 parts by weight of acetone
1.5 parts by weight of dimethylformamide
Emulsifier: 0.5 part by weight of alkylaryl polyglycol ether An appropriate preparation of active compound is prepared by mixing 1 part by weight of active compound with the stated amounts of solvents and emulsifier and diluting the concentrate with emulsifier-containing water to the desired concentration.

Dwarf bean leaves (*Phaseolus vulgaris*) populated with a mixed population of the two-spotted spider mite (*Tetranychus urticae*) are treated by spraying with the active compound preparation at the desired concentration.

After the desired time has elapsed a determination is made of the kill level in %. 100% here means that all of the spider mites have been killed; 0% means that no spider mites have been killed. The kill rates found are calculated by the Colby formula.

In this test a synergistically boosted activity as compared with the active compounds applied individually is found for the following active compound combination in accordance with the present application:

TABLE D

Phytopathogenic mites
*Tetranychus urticae* test

| Active compound | Concentration in g/ha | Kill rate in % after $2^d$ |
|---|---|---|
| Cyenpyrafen | 0.8 | 80 |
| Spirodiclofen | 0.8 | 10 |
| Cyenopyrafen + Spirodiclofen (1:1) | | |
| inventive | found* | calc.** |
| | 0.8 + 0.8 | 100 82 |
| Cyflumetofen | 0.8 | 20 |
| Spirodiclofen | 0.8 | 10 |
| Cyflumetofen + Spirodiclofen (1:1) | | |
| inventive | found* | calc.** |
| | 0.8 + 0.8 | 80 28 |
| Spiromesifen | 0.8 | 10 |

TABLE D-continued

Phytopathogenic mites
*Tetranychus urticae* test

| Active compound | Concentration in g/ha | Kill rate in % after 2$^d$ | |
|---|---|---|---|
| Cyflumetofen + Spiromesifen (1:1) | | | |
| inventive | | found* | calc.** |
| | 0.8 + 0.8 | 60 | 28 |
| IKA 2002 | 0.8 | 0 | |
| Spirotetramat | 0.8 | 0 | |
| IKA 2002 + Spirotetramat (1:1) | | | |
| inventive | | found* | calc.** |
| | 0.8 + 0.8 | 50 | 0 |
| IKA 2002 | 0.032 | 0 | |
| Spiromesifen | 0.16 | 0 | |
| IKA 2002 + Spiromesifen (1:5) | | | |
| inventive | | found* | calc.** |
| | 0.032 + 0.16 | 50 | 0 |

*found = action found
**calc. = action calculated by the Colby formula

EXAMPLE E

Critical Concentration Test/Soil Insects—Treatment of Transgenic Plants

Test insect: *Diabrotica balteata*—larvae in the soil
Solvent: 7 parts by weight of acetone
Emulsifier: 1 part by weight of alkylaryl polyglycol ether An appropriate preparation of active compound is prepared by mixing 1 part by weight of active compound with the stated amount of solvent, adding the stated amount of emulsifier and diluting the concentrate with water to the desired concentration.

The preparation of active compound is poured onto the soil. The concentration of the active compound in the preparation is virtually irrelevant here, the only critical factor being the amount by weight of active compound per unit volume of soil, which is stated in ppm (mg/l). The soil is introduced into 0.25 l pots, which are left to stand at 20° C.

Immediately after sample preparation, 5 pregerminated maize corns of the cultivar YIELD GUARD (trademark of Monsanto Comp., USA) are placed in each pot. After 2 days the corresponding test insects are placed into the treated soil. After a further 7 days the efficacy of the active compound is determined by counting the maize plants that have emerged (emergence of all plants=100% action).

EXAMPLE F

*Heliothis virescens* Test—Treatment of Transgenic Plants

Solvent: 7 parts by weight of dimethylformamide
Emulsifier: 1 part by weight of alkylaryl polyglycol ether An appropriate preparation of active compound is prepared by mixing 1 part by weight of active compound with the stated amount of solvent and the stated amount of emulsifier and diluting the concentrate with water to the desired concentration.

Soya shoots (*glycine max*) of the cultivar Roundup Ready (trademark of Monsanto Comp. USA) are treated by spraying with the preparation of active compound at the desired concentration and are populated with the tobacco budworm *Heliothis virescens* while the leaves are still moist After the desired time the kill level of the insects is determined.

EXAMPLE G

*Myzus persicae* Test—Treatment of Transgenic Plants

Solvent: 7 parts by weight of acetone
Emulsifier: 2 parts by weight of alkylaryl polyglycol ether An appropriate preparation of active compound is prepared by mixing 1 part by weight of active compound with the stated amount of solvent and the stated amount of emulsifier and diluting the concentrate with water to the desired concentration.

Transgenic cabbage plants (*Brassica oleracea*) heavily infested by the green peach aphid *Myzus persicae* are treated by spraying with the preparation of active compound at the desired concentration.

After the desired time the kill level of the insects is determined.

The invention claimed is:

1. An active compound combination comprising synergistically effective amounts of:
   (a) a first compound selected from the group consisting of spirodiclofen, spiromesifen, and spirotetramat,
   (b) at least one second compound selected from the group consisting of cyenopyrafen, cyflumetofen, and IKA 2002, and
   (c) optionally an extender, a surfactant, or a combination thereof,
   wherein the first compound and the at least one second compound are the only active compounds.

2. The active compound combination according to claim 1, wherein the first compound is spirodiclofen.

3. The active compound combination according to claim 1, wherein the first compound is spiromesifen.

4. The active compound combination according to claim 1, wherein the first compound is spirotetramat.

5. A method of controlling animal pests, comprising applying the active compound combination according to claim 1 to animal pests and/or their habitat.

6. A process for preparing an insecticidal and/or acaricidal composition, comprising mixing the first compound and the at least one second compound according to claim 1 with an extender, a surfactant, or a combination thereof.

7. The active compound combination according to claim 1, wherein the ratio of the first compound to the at least one second compound is from 25:1 to 1:25.

8. The active compound combination according to claim 7, wherein the ratio of the first compound to the at least one second compound is from 10:1 to 1:10.

9. The active compound combination according to claim 8, wherein the ratio of the first compound to the at least one second compound is from 5:1 to 1:5.

10. The active compound combination according to claim 4, wherein the ratio of spirotetramat to the at least one second compound is from 25:1 to 1:25.

11. The active compound combination according to claim 10, wherein the ratio of spirotetramat to the at least one second compound is from 10:1 to 1:10.

12. The active compound combination according to claim 11, wherein the ratio of spirotetramat to the at least one second compound is from 5:1 to 1:5.

* * * * *